United States Patent [19]

Lane

[11] 3,935,280

[45] Jan. 27, 1976

[54] REDUCTION OF AMINO ACIDS IN THE PRESENCE OF BORON TRIFLUORIDE

[75] Inventor: Clinton F. Lane, Milwaukee, Wis.

[73] Assignee: Aldrich-Boranes, Inc., Milwaukee, Wis.

[22] Filed: Jan. 10, 1975

[21] Appl. No.: 540,007

[52] U.S. Cl. .... 260/618 H; 260/638 N; 260/643 G; 260/606.5 B
[51] Int. Cl.[2] ......................................... C07C 29/00
[58] Field of Search ..................... 260/638 N, 618 H

[56] References Cited
UNITED STATES PATENTS

| | | | |
|---|---|---|---|
| 2,856,428 | 10/1958 | Brown............................ | 260/618 H |
| 2,874,165 | 2/1959 | Brown............................ | 260/618 H |
| 3,026,329 | 3/1962 | Brown et al. .................. | 260/618 H |

FOREIGN PATENTS OR APPLICATIONS

| | | | |
|---|---|---|---|
| 795,131 | 5/1958 | United Kingdom............. | 260/618 H |
| 1,319,705 | 1/1963 | France........................... | 260/638 N |

OTHER PUBLICATIONS

Schecter et al., "J. Am. Chem. Soc.", Vol. 74, No. 14, (1952), pp. 3664–3668.

*Primary Examiner*—Joseph E. Evans
*Attorney, Agent, or Firm*—Merriam, Marshall, Shapiro & Klose

[57] ABSTRACT

Organic compounds containing both an amino group and a carboxylic acid group are reduced when treated with boron trifluoride followed by diborane, a borane-ether or borane-organic sulfide complex. The presence of the boron trifluoride is responsible for an increase in the rate of reduction of the carboxylic acid group and eliminates the need for the large excess of the borane complex normally required due to the competing formation of boron-nitrogen compounds. Hydrolysis of the reaction mixture provides a useful and convenient method for separating the corresponding amino alcohol.

8 Claims, No Drawings

REDUCTION OF AMINO ACIDS IN THE PRESENCE OF BORON TRIFLUORIDE

BACKGROUND OF THE INVENTION

1. Field of Invention

This invention realtes to a novel process for the reduction of organic compounds which contain both an amino group and a carboxylic acid group. More particularly, this invention provides a process for the preparation of amino alcohols whereby an organic compound containing both an amino group and a carboxylic acid group is combined with boron trifluoride in a suitable organic liquid medium and this mixture is then treated with diborane, a borane-ether or a borane-organic sulfide complex. After an appropriate interval of time, the reaction mixture is hydrolyzed to yield the corresponding amino alcohol formed by hydrogenation of the carbxylic acid group.

2. Description of the Prior Art

Diborane, $B_2H_6$, is an exceedingly powerful, but selective hydrogenating agent for functional groups as disclosed by H. C. Brown in U.S. Pat. No. 2,874,165 and in his book [H. C. Brown, *Boranes in Organic Chemistry*, Cornell University Press, Ithaca, new York, 1972].

Diborane is a highly reactive gas which rapidly decomposes on exposure to air and moisture. Consequently, it is difficult to handle. Fortunately, diborane is highly soluble in tetrahydrofuran where it exists as a borane-tetrahydrofuran complex which can be represented by the formula:

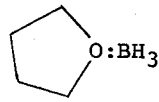

Brown has disclosed in U.S. Pat. No. 3,634,277 a convenient method for preparing and stabilizing solutions of this borane-tetrahydrofuran complex in tetrahdyrofuran.

Borane-tetrahydrofuran has been found to be useful for selective hydrogenations and reductions of organic functional groups [H. C. Brown, P. Heim, and N. M. Yoon, J. Amer. Chem. Soc., 92, 1637 (1970)], and this borane complex has been reported to be particularly useful for the selective reduction of carboxylic acids [N. M. Yoon, C. S. Pak, H. C. Brown, S. Krishnamurthy, and T. P. Stocky, J. Org. Chem., 38, 2786 (1973)].

Borane-dimethyl sulfide is a stable, liquid $BH_3$ complex, and its numerous advantages over the borane-tetrahydrofuran complex have been previously disclosed [L. M. Braun, R. A. Braun, H. R. Crissman, M. Opperman, and R. M. Adams, J. Org. Chem., 36, 2388 (1971)]. The main advantages are that borane-dimethyl sulfide has a molar concentration of borane ten times that of a borane-tetrahydrofuran solution, borane-dimethyl sulfide is soluble in and unreactive toward a wide variety of aprotic solvents, and borane-dimethyl sulfide is apparently stable indefinitely when refrigerated.

Borane-dimethyl sulfide is now commercially available, and its reactivity towards a series of organic functional groups was investigated briefly by Braun and coworkers (supra). Borane-dimethyl sulfide has also been found to be a very useful reagent for the preparation of organoboranes via hydroboration of alkenes [C. F. Lane, J. Org. Chem., 39, 1437 (1974)].

Amino alcohols constitute an important class of organic compounds, many of which are extremely useful synthetic intermediates for the preparation of specialty organic chemicals, pharmaceuticals, and agricultural products. Also, the amino alcohols derived from naturally occurring α-amino acids have been found to be potent, reversible inhibitors of protein synthesis [R. Calendar and P. Berg, Biochemistry, 5, 1690 (1966); D. Cassio, et al., Biochemistry, 6, 827 (1967); P. Rouget and F. Chapeville, European J. Biochem., 4, 305 (1968); B. S. Hansen, et al., J. Biol. Chem., 247, 3854 (1972)]. Consequently, amino alcohols are important and useful chemicals, which presumably should be readily obtainable via reduction of the corresponding amino acids.

Since borane is known to be an effective reagent for the reduction of carboxylic acids [Yoon and coworkers (supra)], it might also be expected that this reagent would be useful for the preparation of amino alcohols via reduction of amino acids. In fact, Yoon and coworkers (supra) have described in detail a procedure for the reduction of p-aminobenzoic acid with borane-tetrahydrofuran and have even suggested this as a general procedure for the reduction of amino acids. Their procedure involves first dissolving the p-aminobenzoic acid in tetrahydrofuran, then treating the resulting solution with borane-tetrahydrofuran. This may indeed be a general procedure for the reduction of those amino acids which have some solubility in tetrahydrofuran but, in general, most amino acids are almost completely insoluble in ether solvents due to zwitterion formation.

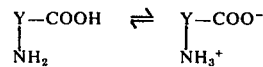

I have found that all of the following amino acids are insoluble in tetrahydrofuran: m-aminobenzoic acid, p-dimethylaminobenzoic acids, leucine, valine, serine, tyrosine, methioniine, alanine, histidine, lysine, glutamic acid, aspartic acid, and 6-aminocaproic acid. The addition of borane-tetrahydrofuran to the above amino acids in slurries at 20°–25°C results in only an extremely slow evolution of hydrogen and the amino acid does not dissolve, indicating that essentially no reduction has occurred. Repeating the above procedure using borane-dimethyl sulfide in place of borane-tetrahydrofuran gives essentially the same result. Also, when this borane-dimethyl sulfide/amino acid/tetrahydofuran slurry is heated to, and maintained at, reflux an increased rate of hydrogen evolution is observed and, in many cases, the amino acid slowly dissolves, indicating an apparent slow rate of reduction.

It has been reported that phenylalaninol (2-amino-3-phenyl-1-propanol) was prepared by reducing phenylalanine with diborane [A. V. Emes and L. C, Vinings, Canadian J. Biochem., 48, 613 (1970)]. However, the experimental details, purity of the product, and yield were not reported. A series of substituted phenylalanines were also recently reported to be reduced by diborane in anhydrous tetrahydrofuran giving good yields of the corresponding substituted phenylalaninols [M. L. Anhoury, et al., J. Chem. Soc. Perkin Transactions I, 191 (1974)]. In both of these cases the starting amino acids must be at least slightly soluble in the tetrahydrofuran.

In addition to the low reactivity of most amino acids due to their insolubility in the common ether solvents used for active hydride reductions, another serious disadvantage is the necessity of using a large excess of the borane reagent to compensate for the active hydrogens on the amino group and for the formation of an unreactive borane-amine complex. Thus, for the reduction of one molar equivalent of an amino acid, one molar equivalent of $BH_3$ is required to reduce the carboxylic acid group, two-thirds of a molar equivalent of $BH_3$ is required for the two active hydrogens on the amino group, and another molar equivalent of $BH_3$ is required for the formation of a borane-amine complex. This means that a total of 2⅔ molar equivalents of $BH_3$ are required to reduce only one molar equivalent of an amino acid, with 1⅔ molar equivalents of $BH_3$ being completely wasted and only one molar equivalent being used for the desired reduction process.

On a small laboratory scale where the value of the amino acid is quite high compared to the cost of the borane reagent, this need for excess borane reagent to accomplish the desired reduction is of small consequence. However, on a commercial scale this added cost of the required extra borane reagent can become quite important. The cost of the excess reagent may, in many cases, be all that is necessary to make the reduction process economiclly unattractive for the production of amino alcohols.

The limitations observed in the direct borane reduction of amino acids due to the insolubility of most amino acids in the ether solvents used for borane reductions and the disadvantage of having to use a large excess of borane reagent to achieve complete reduction of the carboxylic acid group have now been overcome by the use of the present invention.

SUMMARY OF THE INVENTION

The present invention provides a process for reducing a chemical compound, having both a carboxylic acid group and an amino group, whereby the said chemical compound and boron trifluoride are combined or mixed in a suitable liquid organic reaction medium and then combined with diborane, a borane-ether or a borane-organic sulfide reagent.

Advisably, about equivalent molar amounts of the amino acid and boron trifluoride are used, along with an equivalent molar amount of borane in the form of diborane, borane-ether or borane-organic sulfide complex, in this process.

The process is generally carried out at a temperature of about 20°C to 110°C (refluxing toluene). Higher temperatures can be used but the temperature should be sufficiently low so that the boron hydrides do not substantially thermally decompose.

After the compound is reduced, the reaction mixture can be hydrolyzed, such as by heating it in the presence of aqueous alkali. The organic liquid layer is separated from the water layer and the reduced compound is isolated from the organic layer.

The use of this new process eliminates the serious limitation caused by the insolubility of most amino acids in the direct reduction of amino acids with a borane reagent. For example, when borane-dimethyl sulfide is added to a slurry of leucine in tetrahydrofuran at ambient temperatures there is no hydrogen evolution and the amino acid does not go into solution. Essentially no reduction occurs after as long as 24 hours. After heating the reaction mixture at reflux for over seven hours the amino acid goes into solution. However, hydrolysis and isolation of the amino alcohol in the form of a hydrochloride salt gives an impure product which cannot be purified, indicating incomplete reduction. I have now discovered that the reduction of leucine with borane-dimethyl sulfide gives a 71% isolated yield of pure leucinol when the leucine is first reacted with boron trifluoride in tetrahydrofuran at reflux.

Various other amino acids were similarly treated with boron trifluoride in tetrahydrofuran, then heated to reflux with stirring. The boron trifluoride apparently forms a complex with the amino group and the addition of the borane reagent then results in rapid and complete reduction of the carboxylic acid group. Upon hydrolysis with aqueous alkali, the amino-$BF_3$ complex is broken to regenerate the free amino group. This new process thus provides a useful and convenient method for the preparation of amino alcohols.

The use of this new process also eliminates the serious disadvantage present in the old process which required the addition of a large excess of $BH_3$ to compensate for the reactivity of the free amino group. In the new process, presumably, a boron trifluoride-amine complex is formed which does not interfere with the subsequent borane reduction of the carboxylic acid group. Consequently, this new process is quite attractive economically because only one equivalent of $BH_3$ is required per carboxylic acid group to be reduced.

In the practice of the present invention it is important to employ as the liquid medium an organic solvent which does not react with the borane reagent or with the boron trifluoride. Monoethers, polyethers, aromatic hydrocarbons, and saturated aliphatic and alicyclic hydrocarbons can be used for the reaction medium. Although other solvents are suitable, tetrahydrofuran, diethyl ether, diglyme, 1,2-dimethoxyethane, toluene, and various liquid saturated hydrocarbons such as hexane are particularly useful reaction media.

The borane reagent used in the process of the present invention can be either a borane-ether or borane-organic sulfide complex. Diborane gas can also be used but is not recommended due to the extremely hazardous nature of this chemical.

The recommended borane-ether complex is borane-tetrahydrofuran due to its stability and commercial availability. However, other borane-ether complexes, such as borane-diethyl ether, can be employed without any adverse effects.

The borane-organic sulfide complex used in the present invention is prepared by allowing diborane to react with an aliphatic, alicyclic, or cyclic sulfide. Aliphatic sulfides, such as dimethyl sulfide, methylethyl sulfide, diethyl sulfide, methylpropyl sulfide, methylbutyl sulfide, and other lower alkyl sulfides; alicyclic sulfides, such as methylcyclopentyl sulfide and methylcyclohexyl sulfide; cyclic sulfides, such as tetramethylene sulfide, pentamethylene sulfide and heptamethylene sulfide; and disulfides, such as 1,3-dithiomethylpropane, $CH_3SCH_2CH_2CH_2SCH_3$ can be used. The sulfides can contain inert substituents, such as methoxy and methyl groups, as in $CH_3OCH_2CH_2SCH_3$ and 2-methyltetramethylene sulfide. For greatest effectiveness, it is desirable that the molecular weight of the sulfide be low, preferably below 200, so that relatively high molar concentrations can be achieved in the liquid reaction medium. Although a wide variety of organic sulfides can be used, dimethyl sulfide is preferred because of its low molecular weight and its low cost.

The boron trifluoride used in the present invention can be added as a gas to the amino acid/liquid slurry or in the form of its addition compound with an ether, such as diethyl ether, tetrahydrofuran, monoglyme, diglyme, or triglyme, However, boron trifluoride diethyl etherate is the preferred reagent.

DESCRIPTION OF THE PREFERRED EMBODIMENTS

This invention can be further understood by reference to the following examples.

EXAMPLE 1

A dry, 2-liter glass reaction vessel equipped with a pressure-equalizing additon funnel, mechanical stirrer, and reflux condenser vented to a bubbler was charged with 157 grams (1.2 moles) of L-leucine and 0.5 liter of tetrahydrofuran. Boron trifluoride diethyl etherate (0.16 liter, 1.3 moles) when then added dropwise with stirring. When the addition was complete, the reaction mixture was heated to reflux and maintained at reflux for 15 minutes with stirring whereupon the solid went into solution. Gentle heating was then continued as 0.13 liter (1.3 moles) of borane-dimethyl sulfide was added at a rate sufficient to maintain a gentle reflux. Rapid and vigorous gas evolution occurred throughout the addition which took 1.5 hours. Following the addition, the reaction mixture was heated at reflux for an additional 2 hours. An aqueous solution of tetrahydrofuran (0.15 liter of a 1:1 by volume solution) was then added dropwise with stirring and heating followed by 0.64 liter of 6N aqueous sodium hydroxide. After heating at reflux for an additional 2 hours with stirring, the reaction mixture was cooled to room temperature and the upper clear, colorless organic layer was removed. The lower aqueous layer was wahsed with diethyl ether (3 × 0.5 liter) and the combined organic extracts were dried over anhydrous potassium carbonate, filtered, concentrated on a rotary evaporator, and distilled under reduced pressure giving 99.6 grams (71% yield) of L-leucinol, bp 50°C at 0.04 mm, $[\alpha]^{22}_D$ +1.35, $n^{20}_D$ 1.4515, purity by perchloric acid titration: 98%.

EXAMPLE 2

A dry, 12-liter glass reaction vessel equipped as described in Example 1 was charged with 900 grams (7.7 moles) of valine and 2.5 liters of tetrahydrofuran. Using the procedure described in Example 1, boron trifluoride diethyl etherate (1.05 liters, 8.5 moles) was added followed by 0.85 liter (8.5 moles) of borane-dimethyl sulfide at reflux. The addition took 8 hours and heating was continued for an additional 3 hours following the addition. The reaction mixture was then hydrolyzed with 0.75 liter of tetrahydrofuran/water followed by 24.6 moles of sodium hydroxide as an aqueous solution. The product was isolated as described in Example 1 giving 494 grams (62% yield) of 2-amino-3-methyl-1-butanol, bp 78°-79°C at 8 mm, $n^{20}_D$ 1.4543, purity by glc analysis: 97%.

EXAMPLE 3

A dry, 12-liter glass reaction vessel equipped as described in Example 1 was charged with 1.17 kilograms (7.1 moles) of phenylalanine and 3 liters of tetrahydrofuran. Using the procedure described in Example 1, boron trifluoride diethyl etherate (0.96 liter, 7.8 moles) was added followed by 0.78 liter (7.8 moles) of borane-dimethyl sulfide at reflux. The addition took 7 hours and heating was then continued for an additional 3 hours following the addition. The reaction mixture was then hydrolyzed with 0.75 liter of tetrahydrofuran/water followed by 4 liters of 6N aqueous sodium hydroxide solution. The product was isolated as described in Example 1 giving 822 grams (77% yield) of 2-amino-3-phenyl-1-propanol, bp 110°-111°C at 0.10 mm, as a clear, colorless oil which crystallized in the receiver, mp 65°-66°C. The purity by perchloric acid titration was only 93%. The impure amino alcohol was dissolved in 6 liters of tetrahydrofuran and anhydrous hydrogen chloride was added to precipitate the hydrochloride salt which was collected and dried in a vacuum oven giving 940 grams of 2-amino-3-phenyl-1-propanol hydrochloride, mp 147°-151°C, purity by perchloric acid titration: 100%.

EXAMPLE 4

A dry, 5-liter glass reaction vessel equipped as described in Example 1 was charged with 202 grams (1.75 moles) of L-proline and 0.4 liter of tetrahydrofuran. Boron trifluoride diethyl etherate (0.23 liter, 1.84 moles) was then added with external cooling followed by 2.0 liters of a 1M borane-tetrahydrofuran solution at −5°C to 0°C. The addition took 2 hours and stirring was continued overnight in an ice/water bath followed by one hour at reflux. The reaction mixture was then hydrolyzed with 50 milliliters of tetrahydrofuran/water followed by one liter of 6N aqueous sodium hydroxide. The product was isolated as described in Example 1 giving 146 grams of L-prolinol, bp 108°-112°C at 8 mm, $n_D^{20}$ 1.4853, purity by glc analysis: 99%.

EXAMPLE 5

A dry, 22-liter glass reaction vessel equipped as described in Example 1 was charged with 1.44 kilograms (11 moles) of 6-aminocaproic acid and 7 liters of tetrahydrofuran. Using the procedure described in Example 1, boron trifluoride diethyl etherate (1.49 liters, 12.1 moles) was added followed by 1.21 liters (12.1 moles) of borane-dimethyl sulfide at reflux. The addition took 8 hours and heating was maintained overnight following the addition. The reaction mixture was then hydrolyzed with 1.1 liters of tetrahydrofuran/water followed by 5.9 liters of 6N aqueous sodium hydroxide using the procedure described in Example 1. After saturating the aqueous layer with anhydrous potassium carbonate, the organic layer was removed and the aqueous layer was extracted with tetrahydrofuran (4 × 1.5 liters). The combined organic layers were dried over anhydrous potassium carbonate, filtered, and concentrated on a rotary evaporator. The hot, liquid residue was then poured into one liter of hot cyclohexane. After cooling to room temperature, the solid was collected and dried giving 1.0 kilogram (80% yield) of 6-amino-1-hexanol, mp 58°-60°C, with a purity by perchloric acid titration of 99%.

The foregoing detailed description has been given for clearness of understanding only, and no unnecessary limitations should be understood therefrom, as modifications will be obvious to those skilled in the art.

What is claimed is:

1. A process for the reduction of an amino acid to an amino alcohol which comprises contacting a mixture of the said amino acid and boron trifluoride or ether complex thereof with either diborane, a borane-ether complex or a borane-organic sulfide complex.

2. The process of claim 1 wherein a borane-ether complex comprising borane-tetrahydrofuran is used.

3. The process of claim 1 wherein a borane-organic sulfide complex comprising borane-dimethyl sulfide is used.

4. The process of claim 1 wherein the boron trifluoride is used in the form of an ether complex.

5. The process of claim 4 wherein said boron trifluoride ether complex is boron trifluoride diethyl etherate.

6. The process of claim 1 wherein said amino acid and boron trifluoride are mixed in an organic liquid medium selected from the group consisting of monoethers, polyethers, aromatic hydrocarbons, and saturated aliphatic and alicyclic hydrocarbons.

7. The process of claim 1 wherein said amino acid and boron trifluoride are mixed in tetrahydrofuran.

8. The process of claim 1 in which the reaction mixture from the reduction is hydrolyzed and the amino alcohol formed by the reduction is isolated from the hydrolyzed mixture.

* * * * *